United States Patent [19]

Cross et al.

[11] 4,350,696

[45] Sep. 21, 1982

[54] IMIDAZOLE DERIVATIVES, PROCESS FOR THEIR PREPARATION AND PHARMACEUTICAL COMPOSITIONS THEREOF

[75] Inventors: Peter E. Cross, Canterbury; Roger P. Dickinson, Dover, both of England

[73] Assignee: Pfizer Inc., New York, N.Y.

[21] Appl. No.: 235,330

[22] Filed: Feb. 17, 1981

[30] Foreign Application Priority Data

Mar. 8, 1980 [GB] United Kingdom ................ 8008084

[51] Int. Cl.³ .................. C07D 403/12; C07D 417/12; A61K 31/505; A61K 31/415
[52] U.S. Cl. ..................................... 424/251; 424/263; 424/269; 424/270; 544/331; 546/278; 548/195; 548/251
[58] Field of Search ............... 546/278; 548/251, 195; 544/331; 424/269, 270, 263, 251

[56] References Cited

U.S. PATENT DOCUMENTS

| | | | |
|---|---|---|---|
| 3,862,163 | 1/1975 | Boroschewski et al. | 548/195 |
| 4,230,714 | 10/1980 | Cross et al. | 546/278 |
| 4,238,493 | 12/1980 | Roantree et al. | 546/278 |

FOREIGN PATENT DOCUMENTS

2031408 4/1980 United Kingdom .
2038821 7/1980 United Kingdom .
2041363 9/1980 United Kingdom .

*Primary Examiner*—Mary C. Lee

*Attorney, Agent, or Firm*—Charles J. Knuth; Albert E. Frost; Robert K. Blackwood

[57] ABSTRACT

Compounds of the general formula:

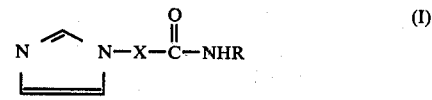

wherein X is a group of the formula:

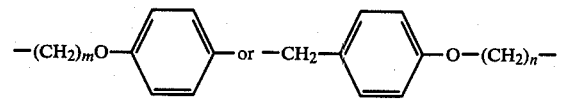

m is 2 or 3; n is an integer of from 1 to 4; and R is a 5-membered heterocyclic group containing as heteroatoms a nitrogen atom and an additional oxygen or sulphur atom or up to three further nitrogen atoms; or a 6-membered heterocyclic group containing one or two nitrogen atoms;

and the pharmaceutically acceptable acid addition salts thereof, are able to selectively inhibit the action of the thromboxane synthetase enzyme without significantly inhibiting the action of the prostacycline synthetase or cyclo-oxygenase enzymes and are thus useful in the treatment of ischaemic heart disease, stroke, transient ischaemic attack, thrombosis, migraine and the vascular complications of diabetes.

10 Claims, No Drawings

IMIDAZOLE DERIVATIVES, PROCESS FOR THEIR PREPARATION AND PHARMACEUTICAL COMPOSITIONS THEREOF

BACKGROUND OF THE INVENTION

This invention relates to imidazole derivatives and in particular to certain imidazolylmethylphenoxyalkanamides and imidazolylalkoxybenzamides substituted on the amide nitrogen with various nitrogen containing heterocyclic groups. Such compounds are able to selectively inhibit the action of the thromboxane synthetase enzyme without significantly inhibiting the action of the prostacyclin synthetase or cyclo-oxygenase enzymes. The compounds are thus useful in, for example, the treatment of thrombosis, ischaemic heart disease, stroke, transient ischaemic attack, migraine and the vascular complications of diabetes.

Our published U.K. patent application No. 2,038,821A describes selective inhibitors of the thromboxane synthetase enzyme which are structurally related amides of the formula

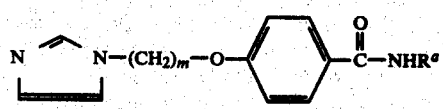

and

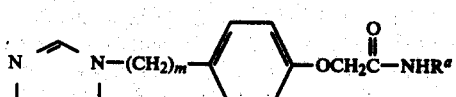

wherein m is 2 or 3 and $R^a$ is hydrogen, $(C_1-C_4)$alkyl, $(C_1-C_4)$alkanoyl, $(C_1-C_4)$alkylsulfonyl, CN, benzoyl or benzenesulfonyl.

Our published U.K. patent application No. 2,041,363A further describes structurally related amides of the formula

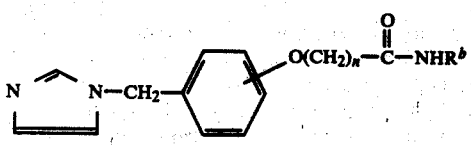

wherein n is 1 to 4 and $R^b$ is hydrogen, $(C_1-C_4)$alkyl or $(C_2-C_4)$alkanoyl.

The above cited U.K. applications and U.K. patent application No. 2,031,408A for "Imidazole Derivatives" by Kenji et al. independently describe acids and esters corresponding to the amides of the present invention. These compounds also possess thromboxane synthetase enzyme inhibiting activity.

SUMMARY OF THE INVENTION

According to the invention there are provided compounds of the general formula:

wherein X is a group of the formula:

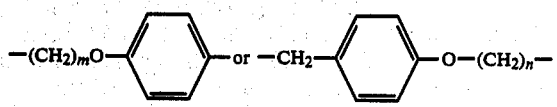

m is 2 or 3; n is an integer of from 1 to 4; and R is a 5-membered heterocyclic group containing as heteroatoms a nitrogen atom and an additional oxygen or sulphur atom or up to three further nitrogen atoms; or a 6-membered heterocyclic group containing one or two nitrogen atoms; and the pharmaceutically acceptable acid addition salts thereof.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound of salt together with a pharmaceutically acceptable diluent or carrier.

The invention also includes a pharmaceutical composition comprising a compound of the formula (I), or a pharmaceutically acceptable salt thereof, together with a pharmaceutically acceptable diluent or carrier.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluene sulphonate salts.

Examples of suitable heterocyclic groups include 2-thiazolyl, 2-pyridyl, 2-pyrimidinyl and 5-tetrazolyl; 2-pyridyl and 2-thiazolyl being preferred.

Preferred values for m and n are 2 and 1 respectively.

DETAILED DESCRIPTION OF THE INVENTION

The compounds of the invention are prepared from the corresponding carboxylic acid of the formula:

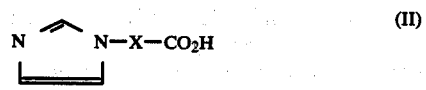

by reacting with an amine of the formula:

$NH_2-R$ 

wherein X and R are as previously defined.

There are various methods of achieving the reaction between the amine and the carboxylic acid and these possibilities and methods for their performance will be well known to those skilled in the art. Generally the acid is converted to an activated derivative, e.g. the acid chloride, imidazolide anhydride or mixed anhydride, prior to reaction with the amine.

Thus in one method the acid is converted to the acid chloride, for example by reacting with thionyl chloride, at room temperature for several hours and after removal of excess thionyl chloride, the resulting acid chloride is taken up in an inert organic solvent, e.g. methylenechloride and the amine added, generally in an equivalent amount or using a slight excess. An organic base e.g., triethylamine is also added with advantage to neutralise the liberated hydrogen chloride. The reaction with the amine is generally complete within several hours at room temperature and the product is then isolated in a conventional manner e.g., by filtration of the product is insoluble in the particular solvent, or by evaporation of the solvent, and the crude product may be further purified, if desired, by recrystallisation or by chromatography.

As an alternative procedure the acid is converted to an activated derivative, e.g., an imidazolide, by reaction with an activating agent such as 1,1-carbonyldiimidazole. In this case the activating agent is added to a solution of the acid in an inert organic solvent e.g., tetrahydrofuran and after a sufficient period of time to ensure formation of the activated intermediate, the amine is added, generally in an amount of 1 equivalent or in a slight excess. The period of time for the reaction to go to completion will naturally depend upon the precise reaction conditions and reagents employed. We have found, however, that when 1,1-carbonyldiimidazole is used as the activating reagent, formation of the required amide is generally complete within a period of 12 hours at room temperature and the reaction may conveniently be performed by stirring overnight. The product is isolated in a conventional manner e.g., by filtration, if insoluble, or by evaporation of the solvent, and the crude product is further purified by solvent extraction and conventional washing techniques and by recrystallisation and chromatography if desired.

The pharmaceutically acceptable salts of the compounds of formula (I) can be prepared by mixing solutions containing equimolar amounts of the free base and appropriate acid and the required salt is collected by filtration, if insoluble, or by evaporation of the solvent.

Preparation of the acids of formula (II) is described in our British Patent Specifications Nos. 2038821A and 2041363A.

The compounds of formula (I) have been found to selectively inhibit the action of the thromboxane synthetase enzyme without significantly affecting the action of the prostacyclin synthetase or cyclo-oxygenase enzymes. Thus the compounds are of value in the treatment of a variety of clinical conditions which are characterised by an inbalance of prostacyclin/thromboxane $A_2$. For the reasons given below these conditions include thrombosis, ischaemic heart disease, stroke, transient ischaemic attack, migraine and the vascular complications of diabetes.

Research work has established that in most tissues the major product of the arachidonic acid metabolism is either of two unstable substances, thromboxane $A_2(TxA_2)$ or prostacyclin $(PGI_2)$. (Proc. Nat. Acad. Sci. U.S.A., 1975, 72, 2994; Nature, 1976, 263, 663; Prostaglandins, 1976, 12, 897). In most cases the prostaglandins $PGE_2$, $PGF_{2\alpha}$ and $PGF_2$ are comparatively minor by-products in this bio-synthetic pathway. The discovery of thromboxane $A_2$ and prostacyclin has significantly increased our understanding of vascular homeostasis, prostacyclin for instance is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685; Science, 1976, 17; Nature, 1978, 273, 765.)

Thromboxane $A_2$ is synthetised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18; Prostaglandins, 1978, 13, 3.) Alteration of the prostacyclin/thromboxane balance in favour of the latter substance could result in platelet aggregation, vasospasm (Lancet, 1977, 479; Science, 1976, 1135; Amer. J. Cardiology, 1978, 41, 787) and an increased susceptibility to atherothrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. Aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extra-cerebral blood flow, in particular a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only is an abnormality of platelet function a major factor in the pathogenesis of migraine attacks but it is in fact their prime cause (Lancet (ii), 1978, 501). Thus a drug that selectively modifies platelet function to inhibit thromboxane $A_2$ formation could be of considerable benefit in migraine therapy.

Abnormalities of platelet behaviour have also been reported in patients with diabetes mellitus (Metabolism, 1979, 28, 394; Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds U.K., April 1979). Also it has been shown that in rats with experimental diabetes vascular prostacyclin production is impaired and TxA$_2$ synthesis from the platelets is elevated (IV International Prostaglandin Conference, Washington, D.C. May 1979). Thus the imbalance between prostacyclin and TxA$_2$ is considered to be responsible for the microvascular complications of diabetes. A TxA$_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the PGG$_2$/H$_2$ endoperoxides and by so doing to reduce both the prostacyclin and thromboxane A$_2$ levels. Aspirin and aspirin-like drugs have been evaluated clinically for prevention of stroke and heart attack (New England and J. Med. 1978, 299, 53; B.M.J. 1978, 1188; Stroke, 1977, 8, 301) and some encouraging results have been obtained. However, it is clear that a compound which specifically inhibits thromboxane A$_2$ formation leaving the biosynthesis of prostacyclin unimpaired would be more valuable in these clinical conditions (Lancet (ii), 1978, 780).

The effect of the compounds of the formula (I) on the thromboxane synthetase enzyme, and the prostacyclin synthetase and cyclo-oxygenase enzymes has been measured by the following in vitro enzyme assays:

1. Cyclo-oxygenase

Ram seminal vesicle microsomes (Biochemistry, 1971, 10, 2372) are incubated with arachidonic acid (100 $\mu$M: 1 min.: 22° C.) to product PGH$_2$ and aliquots of the reaction mixture injected into a stream of Krebs-bicarbonate at 37° C. containing a mixture of antagonists (Nature, 1978, 218, 1135) and indomethacin (Brit. J. Pharmacol., 1972, 45, 451) which is superfusing a spirally cut rabbit aorta strip (Nature 1969, 223, 29). The ability of a compound to inhibit the enzyme is measured by comparing the increases in isometric tension produced by PGH$_2$ in the absence of the test compound, and following pre-incubation of the enzyme with the test compound for 5 minutes.

2. Prostacyclin (PGI$_2$) Synthetase

Pig aorta microsomes (Nature, 1976, 263, 663) are incubated (30 sec.: 22° C.) with PGH$_2$ produced as in 1 and aliquots bio-assayed as in 1. PGI$_2$ production is assessed indirectly by measuring the decrease in PGH$_2$-induced tension (PGI$_2$ itself does not contract the aorta). This decrease can be prevented completely by pre-incubation of the enzyme with the selective PGI$_2$ synthetase inhibitor, 15-hydroperoxy-arachidonic acid (Prostaglandins, 1976, 12, 715). The test compound is then pre-incubated with the enzyme for 5 minutes, and its ability to prevent the decrease in tension is measured.

3. Thromboxane A$_2$ (TxA$_2$) Synthetase

Indomethacin pre-treated human platelet microsomes (Science 1976, 193, 163) are incubated (2 min.: 0° C.) with PGH$_2$ (produced as in 1) and aliquots of the reaction mixture superfused over two rabbit aorta spirals which are separated by a delay coil (2 min.). The latter is required to allow the selective decay of the more unstable thromboxane A$_2$ (Proc. Nat. Acad. Sci., 1975, 72, 2994) thereby enabling the separate measurement of increased isotension due to the TxA$_2$ formed and the PGH$_2$ remaining. The test compound is pre-incubated with the enzyme for 5 minutes, and its ability to inhibit the thromboxane synthetase enzyme is measured as its reduction of the TxA$_2$ component of the isometric tension.

Compounds of the invention tested in this way have been shown to be capable of selectively inhibiting the thromboxane synthetase enzyme.

In addition to the above, an in vitro assay for measuring the inhibition of human blood platelet aggregation has been described and this may be predictive of anti-thrombotic efficacy clinically (Lancet (ii), 1974, 1223; J. Exp. Med., 1967, 126, 171). Both clinically effective agents, aspirin and sulphinpyrazone show inhibitory activity in vitro against a variety of aggregating agents in this test.

A number of in vivo tests in animals have also been described for evaluating potential anti-thrombotic drugs. Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138).

The compounds can be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to give tablets of the desired size. Capsules are typically prepared by granulating the ingredients together and filling them into hard gelatine capsules of the appropriate size to contain the desired dosage.

The compounds can also be administered parenterally, for example by intramuscular, intravenous or subcutaneous injection. For parenteral administration, they are best used in the form of a sterile aqueous solution which can contain other solutes such as tonic and pH adjusters. The compounds can be added to distilled water and the pH adjusted to 3–6 using an acid such as citric, lactic or hydrochloric acid. Sufficient solutes such as dextrose or saline can be added to render the solution isotonic. The resulting solution can then be sterilised and filled into sterile glass vials of an appropriate size to contain the desired volume of solution. The compounds of the invention can also be administered by the infusion of a parenteral formulation as described above into a vein.

For oral administration to human patients, the daily dosage level of a compound of the invention will be from 0.1 to 20 mg/kg per day for a typical adult patient (70 kg). For parenteral administration, the daily dosage level of a compound of the formula (I) will be from 0.01–0.5 mg/kg per day for a typical adult patient. Thus tablets or capsules will generally contain from 5 to 150 mg of the active compound for administration orally up to 3 times a day. Dosage units for parenteral administration can be expected to contain from 0.5–35 mg of the active compounds. A typical vial is a 10 ml vial containing 5 mg of the active compound in 6–10 ml of solution.

It should of course be appreciated that the physician in any event will determine the actual dosage which will be most suitable for the individual and it will vary with the age, weight and response of the patient. The above dosages are exemplary of the average patient; there may of course be individual cases where higher or lower dosage ranges are merited.

The preparation of compounds of the invention is illustrated by the following Examples:

EXAMPLE 1

2-[4-(1-Imidazolylmethyl)phenoxyacetamido]pyridine 1,1'-Carbonyldiimidazole (1.2 g) was added to a solution of 1-(4-carboxymethoxybenzyl)imidazole hydrochloride (2.0 g) in tetrahydrofuran (25 ml) and N,N-dimethylformamide (50 ml), and the mixture was stirred at room temperature for 2½ hours. 2-Amino-pyridine (0.76 g) was added and the stirring continued for a further 12 hours at room temperature. The solvents were evaporated, the residue treated with 5% aqueous sodium bicarbonate solution (100 ml) and the mixture extracted with chloroform (3×75 ml). The combined extracts were washed with water, dried over $MgSO_4$ and evaporated to yield an oil which solidified on standing. Recrystallisation from toluene afforded the amide (1.2 g), m.p. 109°–110° C. Found: C, 66.19; H, 5.19; N, 17.89; $C_{17}H_{16}N_4O_2$ requires: C, 66.22; H, 5.23; N, 18.17%.

EXAMPLES 2–4

The following compounds were prepared by the general method of Example 1 but using the appropriate amine instead of 2-aminopyridine.

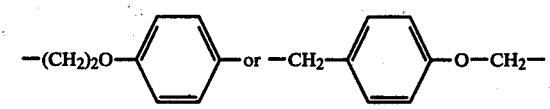

| Example | R | M.P. °C. | Analysis % (Theoretical in brackets) | | |
|---|---|---|---|---|---|
| | | | C | H | N |
| 2 | 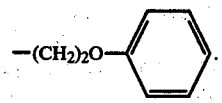 | 160–162 | 56.96 (57.31 | 4.52 4.49 | 17.78 17.82) |
| 3 | 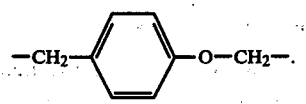 | 172–174 | 61.79 (62.12 | 5.45 4.89 | 22.83 22.64) |
| 4 | 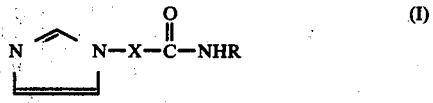 | 238–240 | 50.93 (50.64 | 4.46 4.58 | 31.62 31.81)* |

*Hemihydrate

EXAMPLE 5

1-[[2-[4-(N-Tetrazol-5-yl-carbamoyl)phenoxy]ethyl]]imidazole

1-[2-(4-Carboxyphenoxy)ethyl imidazole] (0.75 g) was added portionwise to thionyl chloride (10 ml) and the mixture stirred at room temperature for 1½ hours. Excess thionyl chloride was evaporated under vacuum and the residual oil was dissolved in methylenechloride (10 ml) and stirred at room temperature while a solution of 5-aminotetrazole (0.25 g) in triethylamine (5 ml) was added. The mixture was stirred for a further 12 hours and the solid product was collected by filtration and recrystallised from ethanol to give the product (0.15 g), m.p. 263° C. Found: C, 51.99; H, 4.70; N, 32.62. $C_{13}H_{13}N_7O_2$ requires: C, 52.17; H, 4.38; N, 32.76%.

We claim:

1. A compound of the general formula:

$$N\!\!\frown\!\!N-X-\overset{O}{\overset{\|}{C}}-NHR \quad (I)$$

wherein X is a group of the formula:

$$-(CH_2)_2O-\!\!\bigcirc\!\!- \text{ or } -CH_2-\!\!\bigcirc\!\!-O-CH_2-$$

and R is a 2-thiazolyl, 2-pyridyl, 2-pyrimidinyl or 5-tetrazolyl group, and the pharmaceutically acceptable acid addition salts thereof.

2. A compound according to claim 1 wherein X is a group of the formula:

$$-(CH_2)_2O-\!\!\bigcirc\!\!-.$$

3. A compound according to claim 2 wherein R is 5-tetrazolyl, said compound being 1-[[2-[4-(N-tetrazol-5-yl-carbamoyl)phenoxy]ethyl]]imidazole.

4. A compound according to claim 1 wherein X is a group of the formula:

$$-CH_2-\!\!\bigcirc\!\!-O-CH_2-.$$

5. A compound according to claim 4 wherein R is 2-pyridyl, said compound being 2-[4-(1-imidazolylmethyl)phenoxyacetamido]pyridine.

6. A compound according to claim 4 wherein R is 2-thiazolyl, said compound being 2-[4-(1-imidazolylmethyl)phenoxyacetamido]thiazole.

7. A compound according to claim 4 wherein R is 2-pyrimidinyl, said compound being 2-[4-(1-imidazolylmethyl)phenoxyacetamido]pyrimidine.

8. A compound according to claim 4 wherein R is 5-tetrazolyl, said compound being 5-[4-(1-imidazolylmethyl)phenoxyacetamido]tetrazole.

9. A pharmaceutical composition for use as an inhibitor of thromboxane synthetase enzyme, comprising an effective amount of a compound of claim 1 or a pharmaceutically acceptable acid addition salt thereof together with a pharmaceutically acceptable diluent or carrier.

10. A method of selectively inhibiting the thromboxane synthetase enzyme in an animal which comprises administering an effective amount of a compound of claim 1 or a pharmaceutically acid addition salt thereof or of a pharmaceutical composition of claim 9.

* * * * *